US006235673B1

(12) United States Patent
Zoeller et al.

(10) Patent No.: US 6,235,673 B1
(45) Date of Patent: May 22, 2001

(54) CARBONYLATION CATALYST SUPPORTED ON A CARBONIZED POLYSULFONATED DIVINYLBENZENE-STYRENE COPOLYMER

(75) Inventors: Joseph Robert Zoeller; Andy Hugh Singleton; Gerald Charles Tustin, all of Kingsport; Donald Lee Carver, Church Hill, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/543,772

(22) Filed: Apr. 5, 2000

(51) Int. Cl.$^7$ .............................. B01J 31/00; B01J 27/06; B01J 27/128; B01J 23/40; B01J 23/58

(52) U.S. Cl. .......................... 502/159; 502/224; 502/229; 502/326; 502/327; 502/328; 502/330

(58) Field of Search .................................... 502/159, 224, 502/229, 326, 328, 327, 330

(56) References Cited

U.S. PATENT DOCUMENTS 3,689,533 9/1972 Schultz .
3,717,670 2/1973 Schultz .
4,040,990 * 8/1977 Neely ..................................... 521/29
4,235,744 * 11/1980 Pesa et al. ........................... 502/161
4,328,125 5/1982 Drago et al. .
4,413,151 * 11/1983 Michaelson et al. ................ 568/860
4,417,077 11/1983 Drago et al. .
4,667,053 * 5/1987 Lin ....................................... 560/204
4,776,987 10/1988 Luft et al. .
4,839,311 6/1989 Maroldo et al. .
5,144,068 9/1992 Smith et al. .
5,155,261 10/1992 Marston et al. .
5,300,685 * 4/1994 Scates et al. ......................... 562/608
5,352,813 * 10/1994 Cavell et al. .......................... 556/21
5,360,929 11/1994 Watston .
5,364,963 * 11/1994 Minami et al. ...................... 562/519
5,488,143 1/1996 Uhm et al. .
5,510,524 4/1996 Garland et al. .
5,900,505 5/1999 Tustin et al. .
5,942,460 * 8/1999 Garland et al. ...................... 502/150
6,159,896 * 12/2000 Zoeller et al. ....................... 502/326
6,177,380 * 1/2000 Zoeller et al. ....................... 502/181

FOREIGN PATENT DOCUMENTS 0 120 631 10/1984 (EP) .
0 461 802 12/1991 (EP) .

OTHER PUBLICATIONS

A. Krzywicki and M. Marczewski, "Formation and Evolution of the Active Site for Methanol Carbonylation on Oxide Catalysts Containing $RhCI_3$", *Journal of Molecular Catalysis*, 6 (1979) pp. 431–440, Netherlands.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) pp. 421–429, Netherlands.

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 8, No. 8, (1988) pp. 1315–1320, Great Britain.

M. J. Howard, M. D. Jones, M. S. Roberts and S. A. Taylor, "$C_1$ to Acetyls: Catalysis and Process", *Catalysis Today*, 18 (1993) pp. 325–354, Amsterdam.

* cited by examiner

*Primary Examiner*—Marc L. Bell
*Assistant Examiner*—Patricia L. Hailey
(74) *Attorney, Agent, or Firm*—Mathew Smith; Harry Gwinnell

(57) ABSTRACT

A catalyst in carbonylation processes for producing esters, carboxylic acids, and carboxylic acid anhydrides from lower alkyl alcohols, ethers, esters, alcohol producing derivatives. The catalyst includes a catalytically active metal selected from Group VIII metals, tin mixtures thereof associated with a carbonized polysulfonated divinylbenzene-styrene copolymer.

27 Claims, No Drawings

CARBONYLATION CATALYST SUPPORTED ON A CARBONIZED POLYSULFONATED DIVINYLBENZENE-STYRENE COPOLYMER

FIELD OF THE INVENTION

The present invention relates to a solid phase catalyst that is useful for the carbonylation of alkyl alcohols, ethers and ester-alcohol mixtures to produce esters and carboxylic acids. More particularly, the present invention relates to a supported catalyst which includes a catalytically effective amount of an active metal selected from Fe, Co, Ni, Ru, Rh, Pd, Os, Ir, Pt, and Sn in which the active metal is supported on a carbonized polysulfonated divinylbenzene-styrene copolymer resin. The catalyst is particularly useful for the carbonylation of methanol and its derivatives to produce acetic acid and acetates in a vapor-phase carbonylation process.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers. There has been considerable research activity in the use of metal catalysts for the carbonylation of lower alkyl alcohols, such as methanol, and ethers to their corresponding carboxylic acids and esters Carbonylation of methanol is a well known process for the preparation of carboxylic acids and particularly for producing acetic acid. Such processes are typically carried out in the liquid phase with a catalyst. The prior art teaches the use of a number of catalysts for the synthesis of carboxylic acids by reaction of alcohols with carbon monoxide at elevated temperatures and pressures using a fixed bed reactor in both gas and liquid phase reactions. Generally, the liquid phase carbonylation reaction for the preparation of acetic acid using methanol is performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst.

Currently, the best industrial practices for the carbonylation of methanol to acetic acid uses homogeneous catalysts consisting of either a mixture of rhodium and lithium, as exemplified in U.S. Pat. No. 5,510,524, or a mixture of iridium and ruthenium, as exemplified in European Patent Application EP 0 752 406 A1.

Unfortunately, these catalysts suffer from the typical difficulties associated with the use of homogeneous catalysis. In particular, upon separation of the catalyst and liquid components, catalyst precipitation and volatilization can occur, particularly if one tries to remove most of the liquid component. Further, mass transfer limitations, which are inherent in the transfer of gaseous carbon monoxide into a liquid reaction medium, limit the ultimate achievable rates in these homogeneously catalyzed processes.

U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions.

U.S. Pat. No. 5,510,524 teaches that the addition of rhenium improves the rate and stability of both the Ir-I and Rh-I homogeneous catalyst systems.

European Patent Application EP 0 752 406 A1 teaches that ruthenium, osmium, rhenium, zinc, cadmium, mercury, gallium, indium, or tungsten improve the rate and stability of the liquid phase Ir-I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle, and even higher rates.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

Of these active carbonylation catalysts, carbon based supports are generally substantially better from a rate perspective, with Ni, Sn, and Pb displaying negligible activity on inorganic oxides. The normally large difference in rates upon changing from and activated carbon to an inorganic support has been exemplified in in M. J. Howard, et. al., *Catalysis Today,* 18, 325 (1993), where, on p. 343, a mixed Rh—Ni catalyst on activated carbon support can be compared to a rhodium on inorganic oxides. With the Rh—Ni on activated carbon, the rate is reported as being ca. 5 mol of acetyl/g of Rh/h at 188° C., 9 bar of 1:2 $CO:H_2$, whereas the range for inorganic oxides is only 0.1 to 0.5 mol of acetyl/g of Rh/h despite being operated at substantially higher temperature (220° C.) and substantially higher CO pressures (40 bar CO pressure).

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Nickel on activated carbon has been studied as a heterogeneous catalyst for the halide-promoted vapor phase carbonylation of methanol, and increased rates are observed when hydrogen is added to the feed mixture. Relevant references to the nickel-on-carbon catalyst systems are provided by Fujimoto et al. In *Chemistry Letters* (1987) 895–898 and in *Journal of Catalysis,* 133 (1992) 370–382 and in the references contained therein. Liu et al., in *Ind. Eng. Chem. Res.,* 33 (1994) 488–492, report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general, the rates of reaction provided by nickel-based catalysts are lower than those provided by the analogous rhodium-based catalysts when operated under similar conditions.

A number of solid materials have been reported to catalyze the carbonylation of methanol without the addition of the halide promoter. Gates et al., in *Journal of Molecular Catalysis,* 3 (1977/78) 1–9, describe a catalyst containing rhodium attached to polymer bound polychlorinated thiophenol for the liquid phase carbonylation of methanol. Current, in European Patent Application EP 0 130 058 A1, describes the use of sulfided nickel containing optional molybdenum as a heterogeneous catalyst for the conversion of ethers, hydrogen and carbon monoxide into homologous esters and alcohols.

Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140, describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometallate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase.

Although many of the earlier catalysts are operable in the liquid phase, the active metal is generally rapidly removed from the support by dissolution in the harsh environments associated with carbonylation of methanol and it derivatives. As a consequence, the reaction becomes a homogeneously catalyzed process despite the presence of the support. Further, even if the association of the metal with the carbon support had been retained, the mass transfer limitations are often exacerbated by the introduction of a third phase into the reactor. The presence of a heterogeneous catalyst in a liquid medium forces CO to, not only diffuse into the reaction medium, but, once in the liquid reaction medium, CO must subsequently diffuse from the reaction medium into the heterogeneous catalyst. As a consequence, the reactions above are all preferably operated in the vapor phase where mass transfer is rapid and leaching is negligible.

To overcome the leaching problem, ligands have been used to bind the rhodium to the catalyst support. For example, U.S. Pat. No. 5,155,261 discloses using amines incorporated within the catalyst to retain the rhodium component on a solid support. Generally these functional groups are incorporated either as part of a resin or by grafting to an oxide support. It is now generally understood that these functional groups are quarternized in the process, forming ammonium salts, and the rhodium, which is present as $Rh(CO)_2I_2^-$, is bound by electrostatic attraction.

Unfortunately, although the catalysts containing functional groups have been successful in retarding the leaching of the Rh catalyst into the liquid phase, they still do not overcome the problems associated with diffusion. Further, the functional groups, present as quarternary salts, and the resin backbones are subject to thermal degradation placing strict constraints on the operating temperatures that can be employed with these catalysts. The inability to use higher temperatures with these functionalized catalysts seriously limits the ultimate attainable rates when they are employed in carbonylation processes.

These functionalized catalysts have been primarily designed for liquid phase carbonylation and the operation of the functionalized catalysts in the vapor phase would be expected to be difficult given the poor temperature stability of these functionalized catalysts. The poor temperature stability limits the useful pressures and production rates achievable with these functionalized catalysts. Regardless, one of these functionalized catalysts has been tested in the vapor phase. Unfortunately, the rate was only half that of the corresponding liquid phase process.

The much higher rates associated with metals on activated carbon are commercially attractive for a vapor phase carbonylation process. Unfortunately, carbon has several physical limitations which have inhibited its commercial introduction. Although activated carbon is readily available from a number of commercial sources, its characteristics are highly variable, making the generation of reproducible catalysts difficult. Activated carbon is also brittle and has a poor crush strength. As a consequence, it is subject to rapid physical attrition. These physical limitations have apparently prevented the introduction of a vapor phase carbonylation process using metals supported on activated carbon despite the attractiveness of such a process.

Accordingly, there is a need for a carbonylation catalyst which retains the high activity associated with metal catalysts supported on activated carbon, but has greater structural integrity and uniformity associated with harder supports, such as the inorganic oxides.

SUMMARY OF THE INVENTION

Unexpectedly, it has now discovered that a carbonylation catalyst can be produced by associating a metal selected from Group VIII metals, tin, and combinations thereof with a support comprising carbonized polysulfonated divinylbenzene-styrene copolymers. The catalyst is particularly useful for the carbonylation of methanol to acetic acid, methyl acetate to acetic anhydride, and ethylene to propionic acid (in the presence of water) using either liquid phase or vapor phase carbonylation reaction conditions.

It is an object of the present invention to provide a catalyst composition having an active metal selected from Group VIII metals, tin, and combinations thereof associated with a solid support comprising carbonized polysulfonated divinylbenzene-styrene copolymers that is useful for the carbonylation of reactants selected from lower alkyl alcohols, ethers, lower alcohol derivative sources and mixtures thereof.

It is another object of the present invention to provide a solid phase catalyst composition for vapor phase carbonylation of methanol to form acetic acid and methyl acetate.

It is another object of the invention to provide a method for preparing the catalyst composition of the present invention.

These and other objects and advantages of the invention will become apparent to those skilled in the art from the accompanying detailed description.

DETAILED DESCRIPTION OF THE INVENTION

In accordance with the present invention, a catalyst composition is provided having a catalytically effective amount of an active metal selected from iron, cobalt, nickel, ruthenium, rhodium, palladium, osmium, iridium, platinum, tin and mixtures thereof associated with a carbonized polysulfonated divinylbenzene-styrene copolymer as a support matrix. Optionally, the catalyst may also include a secondary metallic promoter, selected from an alkali, an alkaline earth, lanthanides, gold, mercury, and transition metals selected from the group V, Nb, Ta, Ti, Zr, Hf, Mo, W, and Re, and combinations thereof.

The solid support useful for acting as a carrier for the active metal, and if so utilized the secondary metals described above, is carbonized polysulfonated divinylbenzene-styrene polymers and copolymers having multimodal pore size, including micro and macro pores. Such carbonized polysulfonated divinylbenzene-styrene polymers and copolymers are described in greater detail in U.S. Pat. Nos. 4,839,331, 4,040,990, and 4,265,768 the disclosures of which is incorporated herein by reference. The carbonized polysulfonated divinylbenzene-styrene support matrix is readily available from Rohm and Haas Company, under the tradename AMBERSORB. Advantageously, the carbonized polysulfonated divinylbenzene-styrene polymers impart exceptional physical properties with regard to hardness and brittleness, but still retain the high catalytic activity (rates) associated with softer activated carbons used in carbonylation processes. These advantageous physical properties permit the process to be operated in any of a variety of reactor designs without sustaining serious losses due to physical attrition.

The compound or form of the active metal(s) used to prepare the catalyst generally is not critical and may be selected such complexes as halides, acetates, nitrates, acetonylacetates, and mixtures thereof. For example, when iridium is the active metal, the catalyst may be prepared from any of a wide variety of iridium containing compounds containing a myriad of combinations of halide, trivalent nitrogen, organic compounds of trivalent phosphorous, carbon monoxide, hydrogen, and 2,4-pentane-dione, either alone or in combination. Such materials are available commercially and may be used in the preparation of the catalysts utilized in the present invention. In addition, the oxides of iridium may be used if dissolved in the appropriate medium. Preferably iridium is a salt of one of it chlorides, such as iridium trichloride or hydrated trichloride, hexacholoro-iridate and any of the various salts of hexachloroiridate(IV). One skilled in the art will understand that use of the preferred iridium complexes or other Group VIII and tin metals should be comparable on the basis of cost, solubility, and performance.

Similarly, if so employed, the compound or form of the second metal compound associated with the catalyst generally is not critical, and may be any of a wide variety of compounds containing one or more of the secondary metals. For example, when metals from the Lanthanide Series are used, they may be present either alone or in combination. A wide variety of compounds of these elements containing various combinations of halides, acetates, nitrates, cyclopentadiene, and 2,4-pentane-dione, either alone or in combination, are available commercially and may be used in the preparation of the catalysts utilized in the process of the present invention, including naturally occurring blends of the Lanthanides. In addition, the oxides of these materials may be used if dissolved in the appropriate medium. Desirably, the compound used to provide the second metal is a water soluble form of the metal(s). Preferred sources include acetates, nitrates, and their halides. The most preferred source among these salts would be dictated by its solubility, preferably water solubility, which can vary widely across this list of useful second components. The most preferred secondary metals include lanthanum, cerium, praseodymium, and neodymium (Atomic numbers 57–60), or combinations thereof. The halides of such preferred secondary metals are generally commercially available and water soluble. Activity is still improved and costs are not necessarily prohibitive when the secondary metal is selected from samarium, europium, gadolinium, terbium, dysprosium, holmium, or erbium (atomic numbers 62–68) and mixtures of thereof.

Desirably, the Group VIII and tin and secondary metal is associated with the support material as a result of soluble impregnation of the metals which may result in either a salt of the metals, an oxide of the metals, or a metal in a free state being deposited on the support.

The amount of active metal, and any secondary metal, associated with the support can each vary from about 0.01 weight % to about 10 weight %, with from about 0.05 weight % to about 5 weight % being preferred and from about 0.1 weight percent to about 2 weight percent of each component being more preferred, wherein the aforementioned weight % is based on the total weight of the supported catalyst.

The preparation of associating the active metal, and if so employed the secondary metal, with the solid support is carried out by preferably dissolving or dispersing the Group VIII and tin (and secondary metal component) in a suitable solvent. The liquid used to deliver the active metal, (Group VIII and tin), and secondary metal in the form a solution, dispersion, or suspension typically is a liquid having a low boiling point, i.e., high vapor pressure at a temperature of from about 10° C. to about 140° C. Examples of suitable solvents include carbon tetrachloride, benzene, acetone, methanol, ethanol, isopropanol, isobutanol, pentane, hexane, cyclohexane, heptane, toluene, pyridine, diethylamine, acetaldehyde, acetic acid, tetrahydrofuran and water. The solid support material is then contacted and desirably impregnated with the metal containing solutions. Various methods of contacting the support material with the Group VIII, tin and secondary metal may be employed. For example, an iridium containing solution can be admixed with a secondary metal solution prior to impregnating the support material. Alternatively, the respective solutions can be impregnated separately into or associated with the support material in series fashion. Desirably, in this alternative embodiment, the support is dried prior to contacting the second solution. Similarly, the Group VIII and tin (and secondary metal) may be associated with the support material in a variety of forms such as using slurries of the Group VIII and tin metal (and secondary metal) can be poured over the support material. Alternatively, the support material may be immersed in excess solutions of the active components with the excess being subsequently removed using techniques known to those skilled in the art. The solvent or liquid is evaporated, i.e. the solid support is dried so that at least a portion of the Group VIII and tin (and secondary metal) is associated with the solid support. Drying temperatures can range from about 100° C. to about 600° C. One skilled in the art will understand that the drying time is dependent upon the temperature, humidity, and solvent. Generally, lower temperatures require longer heating periods to effectively evaporate the solvent from the solid support.

Impregnation is only one means for associating the Group VIII and/or tin component with the solid support matrix. Other suitable methods for preparing the solid support component includes sublimation and plasma deposition. These, and other alternative methods of preparation, are familiar to practitioners of the catalysis art.

In addition to the solid support component, the catalyst can also include a halogen promoter as a second component which may also be catalytically active and which aids in the carbonylation process. The halogen promoter includes one or more of chlorine, bromine and/or iodine and preferably, includes bromine and/or iodine which desirably are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide ethyl iodide, 1-iodopropane, 2-iodobutane, 1-iodobutane, methyl bromide, ethyl bromide, and benzyl iodide. Desirably, the halide is a hydrogen halide or an alkyl halide having up to 6 carbon atoms. Non-limiting examples of preferred halides hydrogen iodide, methyl bromide and methyl iodide. The halide may also be a molecular halide such as $I_2$, $Br_2$, or $Cl_2$. The halogen promoter may be introduced at the catalyst preparation step or preferably, is introduced into the carbonylation reactor with the reactants. As a result of contacting the active metal components with the halogen promoter the ultimate active species of the Group VIII and tin and secondary metal may exist as one or more coordination compounds or a halide thereof.

In carrying out the present invention, a mixture, and preferably a gaseous mixture, having lower alkyl alcohols, ethers, derivatives of the desired alcohol feedstock, olefins and mixtures thereof; carbon monoxide and, in a preferred embodiment, a halide are fed to a carbonylation reactor containing the Group VIII metal and tin (and secondary metal, if so utilized) supported catalyst described above. The reactor is maintained under carbonylation conditions of temperature and pressure. The process may be operated to produce high proportions of the carboxylic acid or the ester of the carboxylic acid with the feed of the alcohol to obtain high productivity. For example, if acetic acid is the desired product, the feedstock may consist of methyl alcohol, dimethyl ether, methyl acetate, a methyl halide or any combination thereof. If it is desired to increase the proportion of acid produced, the ester may be recycled to the reactor together with water or introduced into a separate reactor with water to produce the acid in a separate zone.

In a particularly preferred embodiment of the present invention, the catalyst is utilized in a carbonylation process operated in the vapor phase. Accordingly, the carbonylation process is practiced at temperatures above the dew point of the product mixture, i.e., the temperature at which condensation occurs. One skilled in the art understands that the dew point is a complex function of dilution (particularly with respect to non-condensable gases such as unreacted carbon monoxide, hydrogen, or inert diluent gas), product composition, and pressure. Accordingly, the catalyst is useful in processes that may be operated over a wide range of temperatures and pressures. In practice, this generally dictates a temperature range of about 100° C. to 500° C., with temperatures in the range of 100° C. to 325° C. being preferred and temperature of about 150° C. to 300° C. being particularly useful.

The catalyst of the present invention can likewise be utilized in processes operating over a wide range of pressures, depending upon whether the process is operated under liquid-phase or vapor-phase carbonylation conditions. Suitably, process pressures of from about 0.5–500 bar absolute are typical. In the vapor-phase carbonylation process, the pressure range is typically limited by the dew point of the product mixture. Provided that the carbonylation reaction is operated at a temperature sufficient to prevent liquefaction of the product effluent, pressures can range from about 0.1 to 100 bar absolute.

Non-limiting examples of suitable feedstock for carbonylation include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is preferably used in the process and is normally fed as methanol, it can be supplied in the form of a combination of materials which generate methanol. Examples of such combination of materials include (i) methyl acetate and water and (ii) dimethyl ether and water. In the operation of the process, both methyl acetate and dimethyl ether are formed within the reactor and, unless methyl acetate is the desired product, they are recycled with water to the reactor where they are later consumed to form acetic acid. Thus, one skilled in the art will recognize that it is possible to utilize the present invention to produce carboxylic acid from a corresponding ester feed material.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When methyl acetate is the desired product, no water should be added and dimethyl ether becomes the preferred feedstock. Further, when methanol is used as the feedstock in the preparation of methyl acetate, it is necessary to remove water. However, the primary utility of the catalyst of the present invention is in the manufacture of acetic acid.

The present invention is illustrated in greater detail by the specific examples present below. It is to be understood that these examples are illustrative embodiments and are not intended to be limiting of the invention, but rather are to be construed broadly within the scope and content of the appended claims.

In the examples which follow all of the catalysts were prepared in a similar manner except as specified otherwise.

Catalyst 1 (Rh on AMBERSORB 572)

Rhodium (III) chloride hydrate (282 mg, 1.17 mmol of Rh) was dissolved in 30 mL of distilled water and then added to 20.0 grams of AMBERSORB 572 (obtained from Aldrich Chemical Company) in an evaporating dish. (AMBERSORB is a registered trademark of the Rohm and Haas Corp. used for their commercially available carbonized polysulfonated divinylbenzene-styrene copolymer products having 20–50 mesh size and a surface area of 1100 $m^2/g$.). The mixture was heated using a steam bath and stirred continuously until it became free flowing. The material was transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst had a density of 0.47 g/mL and Rh content of 0.55 weight %.

Comparative Catalyst C-1 (Rh On Calgon Activated Carbon)

Rhodium (III) chloride hydrate (282 mg, 1.17 mmol of Ir) was dissolved in 30 mL distilled water and then added to 20.0 grams of 12×40 mesh activated carbon granules, having a BET surface area in excess of 800 $m^2/g$ (obtained from Calgon), contained in an evaporating dish. The mixture was heated using a steam bath and stirred continuously until it became free flowing. The material was transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst (Catalyst C-1) had a density of 0.57 g per mL and Rh content of 0.59 weight %.

Catalyst 2 (Ir on AMBERSORB 572)

Catalyst 2 was prepared in the same manner as described for Catalyst 1, except iridium (III) chloride hydrate (418 mg, 1.17 mmol of Ir) was substituted for the rhodium trichloride hydrate. The catalyst had a density of 0.47 g/mL and an Ir content of 1.02 weight %.

Comparative Catalyst C-2 (Ir on Carbon)

Comparative Catalyst C-2 was prepared in the same manner as described for Comparative Catalyst C-1, except iridium (III) chloride hydrate (418 mg, 1.17 mmol of Ir) was substituted for the rhodium trichloride hydrate. The catalyst (Catalyst C-2) had a density of 0.57 g per mL and an Ir content of 1.1 weight %.

Catalyst 3 (Pt on AMBERSORB 572)

Catalyst 3 was prepared in the same manner as described for Catalyst 1, except chloroplatinic acid hexahydrate ($H_2PtCl_6 \cdot 6H_2O$, 580 mg, 1.17 mmol of Pt) was substituted for the rhodium trichloride trihydrate. The catalyst had a density of 0.47 g/mL and a Pt content of 0.95 weight %.

Comparative Catalyst C-3 (Pt on Carbon)

Comparative Catalyst C-3 was prepared in the same manner as described for Comparative Catalyst C-1, except chloroplatinic acid hexahydrate ($H_2PtCl_6 \cdot 6H_2O$, 580 mg, 1.17 mmol of Pt) was substituted for the rhodium trichloride trihydrate. The catalyst (Catalyst C-3) had a density of 0.57 g per mL and a Pt content of 1.10 weight %.

Catalyst 4 (Sn on AMBERSORB 572)

Tin (II) chloride dihydrate (263 mg, 1.17 mmol of Sn) was dissolved in a solution of 5 mL concentrated hydrochloric acid and 30 mL distilled water. The resultant solution was then added to 20.0 grams of AMBERSORB 572 (obtained from Aldrich Chemical Company) in an evaporating dish. The mixture was heated using a steam bath and continuously stirred until it became free flowing. The material was transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst had a density of 0.47 g/mL and tin content of 0.63 weight %.

Comparative Catalyst C-4 (Sn on Carbon)

Tin (II) chloride dihydrate (282 mg, 1.17 mmol of Ir) was dissolved in a solution of 5 mL concentrated hydrochloric acid in 30 mL of distilled water. The solution was then added to 20.0 g rams of 12×40 mesh activated carbon granules (obtained from Calgon having a BET surface area in excess of 800 $m^2/g$) contained in an evaporating dish. The mixture was heated using a steam bath and stirred continuously until it became free flowing. The material was then transferred to a quartz tube measuring 106 cm long×25 mm (outer diameter). The quartz tube containing the mixture was placed in a three-element electric tube furnace so that the mixture was located in the approximate center of the 61 cm long heated zone of the furnace. Nitrogen was continuously passed through the catalyst bed at a rate of 100 standard cubic centimeters per minute and the tube was heated from ambient temperature to 300° C. over a 2 hour period. The temperature was held at 300° C. for 2 hours. The quartz tube and its contents were allowed to cool back to ambient temperature. The catalyst (Catalyst C-4) had a density of 0.57 g per mL and a Sn content of 0.58 weight %.

Catalyst 5 (2% Rh on AMBERSORB 572)

The preparation of Catalyst 1 was repeated except that the amount of rhodium trichloride hydrate used was raised from 282 mg to 1128 mg. This yielded a catalyst which was 2%Rh on AMBERSORB 572.

Carbonylation Of Methanol—Vapor Phase Process

The reactor system consisted of a 800 to 950 mm (31.5 and 37 inch) section of 6.35 mm (¼ inch) diameter tubing constructed of Hastelloy alloy. The upper portion of the tube constituted the preheat and reaction (carbonylation) zones which were assembled by inserting a quartz wool pad 410 mm from the top of the reactor to act as support for the catalyst, followed sequentially by (1) a 0.7 g bed of fine quartz chips (840 microns), (2) either 1.0 mL (0.47 g) of the AMBERSORB 572 supported catalyst, or 0.5 g (0.88 mL) of the activated carbon supported catalyst in the case of the activated carbon, wherein the preparation of these catalysts appear in the preceding Examples, and (3) an additional 6 grams of fine quartz chips. The top of the tube was attached to an inlet manifold for introducing liquid and gaseous feeds.

The six (6) grams of fine quartz chips acted as a heat exchange surface to vaporize the liquid feeds. Care was taken not to allow any liquid feeds to contact the catalyst bed at any time, including assembly, start-up, operation, and shutdown. The remaining lower length of tubing (product recovery section) consisted of a vortex cooler which varied in length depending on the original length of tubing employed and was maintained at approximately 0–5° C. during operation.

The gases were fed using Brooks flow controllers and liquids were fed using a high performance liquid chromatography pump. The gaseous products leaving the reaction zone were condensed using the vortex cooler described above operating at 0–5° C. The product reservoir was a tank placed downstream from the reactor system. The pressure was maintained using a Tescom 44-2300 Regulator on the outlet side of the reactor system and the temperature of the reaction section was maintained using heating tape on the outside of the reaction system.

Feeding of hydrogen and carbon monoxide to the reactor was commenced while maintaining the reactor at a temperature of 240° C. and a pressure of 17.2 bara (250 psia). The flow rate of hydrogen was set at 25 standard cubic cm. per minute (cc/min) and the carbon monoxide flow rate was set at 100 cc/min. The reactor section was maintained under these conditions for 1 hour or until the temperature and pressure had stabilized (whichever was longer.) The high pressure liquid chromatography pump was then started, feeding a mixture consisting of 70 weight percent methanol and 30 weight percent methyl iodide at a rate of 12 ml/hr (The solution had a density of 1 g/mL.) Samples of the liquid product were collected and analyzed periodically using gas chromatographic techniques.

The comparative examples using activated carbon based catalysts were run in a similar fashion, except they utilized 0.5 grams (0.88 mL) of catalyst.

CARBONYLATION EXAMPLE 1

The composition and weight of the samples taken periodically during the procedure described above in which Catalyst 1, consisting of Rh on AMBERSORB 572, was used are set forth in Table 1 below wherein "Time" is the total time of operation (in hours) of the carbonylation commencing with the feeding of the methanol until a particular sample was taken. The values set forth below "MeI" (methyl iodide), "MeOAc" (methyl acetate), "MeOH" (methanol) and "AcOH" (acetic acid) are weight percentages of each of those compounds present in the sample. The weight of each sample is given in grams.

TABLE 1

| Sample Number | Expired Time (h) | Sample (Wt. %) MeI | MeOAc | MeOH | AcOH | Sample Weight (g) |
|---|---|---|---|---|---|---|
| 1 | 3.50 | 13.32 | 35.38 | 10.95 | 25.17 | 37.2 |
| 2 | 7.50 | 13.54 | 35.54 | 11.02 | 24.98 | 49 |
| 3 | 10.50 | 13.02 | 34.71 | 10.58 | 25.2 | 36.9 |
| 4 | 15.50 | 11.24 | 35.14 | 11.39 | 25.82 | 61.2 |
| 5 | 17.50 | 12.92 | 41.96 | 9.00 | 19.8 | 25.1 |
| 6 | 23.50 | 13.82 | 43.03 | 8.74 | 20.01 | 73.1 |
| 7 | 27.50 | 13.5 | 42.01 | 8.86 | 19.47 | 48.9 |
| 8 | 31.50 | 14.42 | 42.65 | 9.08 | 19.8 | 49.1 |
| 9 | 34.50 | 13.44 | 44.12 | 9.46 | 20.04 | 36.9 |
| 10 | 39.50 | 13.92 | 43.92 | 9.28 | 19.85 | 60.6 |
| 11 | 41.50 | 13.52 | 42.4 | 8.81 | 19.85 | 25.4 |
| 12 | 47.50 | 13.71 | 43.24 | 9.11 | 20.08 | 73.2 |
| 13 | 51.50 | 12.83 | 32.75 | 1.35 | 43.29 | 49.1 |
| 14 | 55.50 | 12.66 | 32.42 | 1.32 | 42.7 | 48.9 |
| 15 | 58.50 | 12.63 | 32.87 | 1.37 | 43.34 | 36.9 |
| 16 | 63.50 | 12.73 | 39.73 | 7.59 | 28.8 | 60.2 |
| 17 | 65.50 | 13.14 | 39.7 | 7.29 | 28.31 | 25.4 |
| 18 | 71.50 | 12.8 | 38.77 | 7.22 | 28 | 73.1 |
| 19 | 75.50 | 13.82 | 40.58 | 7.54 | 29.35 | 49.2 |
| 20 | 79.50 | 12.53 | 38.55 | 7.12 | 27.73 | 24.2 |

The rate of acetyl production based on the preceding experiment utilizing Catalyst 1 is set forth in Table 2 below wherein Sample Number and Time values correspond to those of table 1. "Acetyl Produced" is the amount (millimoles) of methyl acetate and acetic acid produced during each increment of Time calculated from the formula:

Sample Weight×10×((Weight % MeOAc/74)+(Weight % AcOH/60))

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is:

(mmol Acetyl Produced)/(vol. of catalyst (mL)×Time Increment) wherein the volume of catalyst used was 1.0 mL. (Note: the comparative examples, which had a significantly higher density, used 0.88 mL of catalyst.)

TABLE 2

| Sample Number | Expired Time (hours) | Acetyl Produced (mmol) | Rate (mol/L-h) |
|---|---|---|---|
| 1 | 3.50 | 333.9 | 95.4 |
| 2 | 7.50 | 439.3 | 109.8 |
| 3 | 10.50 | 328.1 | 109.4 |
| 4 | 15.50 | 554.0 | 110.8 |
| 5 | 17.50 | 225.2 | 112.6 |
| 6 | 23.50 | 668.9 | 111.5 |
| 7 | 27.50 | 436.3 | 109.1 |
| 8 | 31.50 | 445.0 | 111.3 |
| 9 | 34.50 | 343.2 | 114.4 |
| 10 | 39.50 | 560.2 | 112.0 |
| 11 | 41.50 | 229.6 | 114.8 |
| 12 | 47.50 | 672.7 | 112.1 |
| 13 | 51.50 | 571.6 | 142.9 |
| 14 | 55.50 | 562.2 | 140.6 |
| 15 | 58.50 | 430.4 | 143.5 |
| 16 | 63.50 | 612.2 | 122.4 |
| 17 | 65.50 | 256.1 | 128.1 |
| 18 | 71.50 | 724.1 | 120.7 |
| 19 | 75.50 | 510.5 | 127.6 |
| 20 | 79.50 | 237.9 | 59.5 |

The total production of acetyl products (acetic acid+methyl acetate) over the 79.5 hr. experiment was 9.14 moles representing a space time yield of 115 mol/L-h (245 mol/$kg_{cat}$-h)and a Rh turnover frequency of 76.3 mol of acetyl/mol Rh/min.

Comparative Carbonylation Example C-1

Carbonylation Example 2 was repeated except that 0.5 g of Comparative Catalyst C-1 was used. The results are summarized in Tables 3 and 4.

TABLE 3

| Sample Number | Expired Time (h) | Sample (Wt. %) MeI | MeOAc | MeOH | AcOH | Sample Weight (g) |
|---|---|---|---|---|---|---|
| 1 | 4.00 | 15.27 | 38.87 | 3.4 | 30.27 | 26.9 |
| 2 | 6.00 | 15.86 | 39.8 | 3.46 | 30.93 | 24.9 |
| 3 | 7.00 | 14.36 | 27.85 | 1.29 | 47.57 | 20 |
| 4 | 8.00 | 14.45 | 26.92 | 1.24 | 46.16 | 19.1 |
| 5 | 10.00 | 13.64 | 27.07 | 1.26 | 47.05 | 24.2 |
| 6 | 15.50 | 14.55 | 22.12 | 0.43 | 53 | 90.1 |
| 7 | 17.50 | 14.52 | 22.2 | 0.44 | 53.18 | 29.1 |
| 8 | 23.00 | 13.59 | 11.86 | 0.09 | 65.74 | 85.9 |
| 9 | 25.00 | 13.42 | 11.85 | 0.09 | 65.62 | 28.1 |
| 10 | 27.00 | 13.46 | 12.03 | 0.1 | 66.41 | 26.5 |
| 11 | 29.00 | 14.59 | 15.35 | 0.47 | 62.63 | 25.9 |
| 12 | 31.00 | 13.49 | 14.83 | 0.47 | 61.87 | 25.6 |
| 13 | 33.00 | 13.78 | 16.85 | 0.2 | 60.31 | 25.8 |
| 14 | 34.00 | 14.08 | 16.77 | 0.22 | 60.59 | 8.9 |

TABLE 4

| Sample Number | Expired Time (hours) | Acetyl Produced (mmol) | Rate (mol/L-h) |
|---|---|---|---|
| 1 | 4.00 | 277.0 | 78.9 |
| 2 | 6.00 | 262.3 | 149.5 |
| 3 | 7.00 | 233.8 | 266.6 |
| 4 | 8.00 | 216.4 | 246.7 |
| 5 | 10.00 | 278.3 | 158.6 |
| 6 | 15.50 | 1065.2 | 220.8 |
| 7 | 17.50 | 345.2 | 196.8 |
| 8 | 23.00 | 1078.8. | 223.6 |
| 9 | 25.00 | 352.3 | 200.8 |
| 10 | 27.00 | 336.4 | 191.7 |
| 11 | 29.00 | 324.1 | 184.7 |
| 12 | 31.00 | 315.3 | 179.7 |
| 13 | 33.00 | 318.1 | 181.3 |
| 14 | 34.00 | 110.0 | 125.5 |

The total production of acetyl products (acetic acid+methyl acetate) over the 34.0 hr experiment was 5.51 moles representing a space time yield of 184 mol/L-h (322 mol/$kg_{cat}$-h) and a Rh turnover frequency of 94.2 mol of acetyl/mol Rh/min.

CARBONYLATION EXAMPLE 2

Carbonylation Example 1 was repeated except that Catalyst 2 (1.1% Ir on AMBERSORB 572) was used in place of Catalyst 1. The process was operated for 58.5 hours and generated 4.68 moles of acetyl products, representing a space time yield of 80 mol/L-h (170 mol/$kg_{cat}$-h) and an Ir turnover frequency of 50.2 mol of acetyl/mol Ir/min.

Comparative Carbonylation Example C-2

Comparative Carbonylation Example C-1 was repeated using Comparative Catalyst C-2 (1.1 % Ir on carbon) instead of Comparative Catalyst C-1. The process was operated for 180 hours and generated 8.65 moles of acetyl products, representing a space time yield of 55 mol/L-h (96 mol/$kg_{cat}$-h) and an Ir turnover frequency of 28.0 mol of acetyl/mol Ir/min.

CARBONYLATION EXAMPLE 3

Carbonylation Example 1 was repeated except that Catalyst 3 (0.95% Pt on AMBERSORB 572) was used in place of Catalyst 1. The process was operated for 71 hours and generated 0.95 moles of acetyl products, representing a space time yield of 13.4 mol/L-h (28.5 mol/$kg_{cat}$-h) and a Pt turnover frequency of 9.1 mol of acetyl/mol Pt/min.

Comparative Carbonylation Example C-3

Comparative Carbonylation Example C-1 was repeated using Comparative Catalyst C-3 (Pt on carbon) instead of Comparative Catalyst C-1. The process was operated for 50 hours and generated 2.23 moles of acetyl products, representing a space time yield of 45 mol/L-h (89 mol/$kg_{cat}$-h) and a Pt turnover frequency of 26.4 mol of acetyl/mol Pt/min.

CARBONYLATION EXAMPLE 4

Carbonylation Example 1 was repeated, except that Catalyst 4 (0.63% Sn on AMBERSORB 572) was used in place of Catalyst 1. The results of this carbonylation example are summarized in Tables 5 and 6.

TABLE 5

| Sample Number | Expired Time (h) | Sample (Wt. %) MeI | MeOAc | MeOH | AcOH | Sample Weight (g) |
|---|---|---|---|---|---|---|
| 1 | 3.50 | 18.31 | 0.97 | 72.64 | 3.06 | 35.9 |
| 2 | 7.50 | 19.61 | 0.97 | 76.73 | 3.16 | 50.1 |
| 3 | 10.50 | 17.96 | 1 | 74.8 | 3.15 | 37.1 |
| 4 | 15.50 | 16.71 | 1.03 | 75.53 | 3.1 | 61.9 |
| 5 | 17.50 | 22.25 | 5.89 | 68.93 | 0.43 | 25.1 |
| 6 | 23.50 | 22 | 6.01 | 67.46 | 0.5 | 72.9 |
| 7 | 27.50 | 21.53 | 5.78 | 64.51 | 0.44 | 48.9 |
| 8 | 31.50 | 21.9 | 5.92 | 67.81 | 4.55 | 48.3 |
| 9 | 34.50 | 22.38 | 5.97 | 68.26 | 4.58 | 36.5 |
| 10 | 39.50 | 20.87 | 5.89 | 65.77 | 4.35 | 60.2 |
| 11 | 41.50 | 20.51 | 5.8 | 68.94 | 4.49 | 25.1 |
| 12 | 47.50 | 21.62 | 6.12 | 69.02 | 4.71 | 73.5 |
| 13 | 51.50 | 6.8 | 5.41 | 79.95 | 0.64 | 49.3 |
| 14 | 55.50 | 21.89 | 11.13 | 62.79 | 0.85 | 49.6 |
| 15 | 58.50 | 22.35 | 11.35 | 62.88 | 0.84 | 36.7 |
| 16 | 63.50 | 21.36 | 10.91 | 60.67 | 0.82 | 62.2 |
| 17 | 65.50 | 21.15 | 12.14 | 59.63 | 0.64 | 25.6 |
| 18 | 71.50 | 20.71 | 11.99 | 59.17 | 0.61 | 72.9 |
| 19 | 75.50 | 20.37 | 11.89 | 58.11 | 0.59 | 49.1 |

TABLE 6

| Sample Number | Expired Time (hours) | Acetyl Produced (mmol) | Rate (mol/L-h) |
|---|---|---|---|
| 1 | 3.50 | 23.0 | 6.6 |
| 2 | 7.50 | 33.0 | 8.2 |
| 3 | 10.50 | 24.5 | 8.2 |
| 4 | 15.50 | 40.6 | 8.1 |
| 5 | 17.50 | 21.8 | 10.9 |
| 6 | 23.50 | 65.3 | 10.9 |
| 7 | 27.50 | 41.8 | 10.4 |
| 8 | 31.50 | 75.3 | 18.8 |
| 9 | 34.50 | 57.3 | 19.1 |
| 10 | 39.50 | 91.6 | 18.3 |
| 11 | 41.50 | 38.5 | 19.2 |
| 12 | 47.50 | 118.5 | 19.7 |
| 13 | 51.50 | 41.3 | 10.3 |
| 14 | 55.50 | 81.6 | 20.4 |
| 15 | 58.50 | 61.4 | 20.5 |
| 16 | 63.50 | 100.2 | 20.0 |
| 17 | 65.50 | 44.7 | 22.4 |
| 18 | 71.50 | 125.5 | 20.9 |
| 19 | 75.50 | 83.7 | 20.9 |

This catalyst was unique among all the carbonylation and comparative carbonylation examples in that it displayed an induction period and did not reach a steady production rate until the catalyst was in use for nearly 28 hours. After reaching steady state, the reaction was operated for an additional 48 hours, producing 0.920 moles of acetyl units, representing a space time yield of 19.2 mol/l-h (40.8 mol/$kg_{cat}$-h) and a tin turnover frequency of 13.9 mol of acetyl/mol Sn/min.

Comparative Carbonylation Example C-4

Comparative Carbonylation Example C-1 was repeated using Comparative Catalyst C-4 (Sn on carbon) instead of Comparative Catalyst C-1. The process was operated for 34.5 hours and generated 2.05 moles of acetyl products, representing a space time yield of 68 mol/L-h (118 mol/$kg_{cat}$-h) and an tin turnover frequency of 40.5 mol of acetyl/mol Sn/min.

Carbonylation Of Methyl Acetate—Liquid Phase Process

Two grams (2 gr.) of Catalyst 5 (2%Rh on AMBERSORB 572) was added to a 300 mL Hastelloy®-C autoclave equipped with a magneto-stirrer followed by a solution of 55.5 grams (0.75 mol) of methyl acetate, 11.85 g (0.083 mol) of methyl iodide, and 17.5 g of acetic acid. The autoclave was sealed and pressure tested to 68 atm. with 5% $H_2$ in CO. The autoclave was then vented and pressurized to 6.8 atm with 5% $H_2$ in CO, the stirrer started, and the autoclave was heated to 190° C. Upon reaching the desired temperature, the pressure was adjusted to 34.0 atm using 5% $H_2$ in CO. The pressure was maintained by feeding 5% $H_2$ in CO gas upon demand. These pressures and temperatures were maintained for a period of 8 hrs. Afterwards, the autoclave was cooled to room temperature and slowly vented. The autoclave was opened and the liquid components were removed under vacuum using a "dip-stick" consisting of a glass tube which had been fitted with a course fritted glass filter at its end and which was then connected to a slightly evacuated collection flask. The liquid in the collection vessel was analyzed by gas chromatography.

To demonstrate that the heterogeneous catalyst could be successfully recycled, a fresh charge of the solution of the solution of 55.5 g methyl acetate, 17.5 g acetic acid, and 11.85 g methyl iodide was added to the solid, which remained in the autoclave after product removal. The autoclave was then resealed and the reaction again conducted in a manner identical as that used for the first charge. The product was removed as above and again analyzed by GC. This process was repeated until the catalyst had been used in the carbonylation process a total of 20 times. The results for the GC analyses are compiled in Table 7. Constitutent "Ac2O" is acetic anhydride.

TABLE 7

| Charge | GC Analysis (weight %) | | | |
|---|---|---|---|---|
| No. | MeI | MeOAc | AcOH | Ac2O |
| 1 | 9.53 | 33.36 | 24.86 | 29.96 |
| 2 | 9.58 | 34.18 | 26.78 | 27.46 |
| 3 | 9.45 | 38.26 | 25.29 | 24.69 |
| 4 | 10.08 | 41.74 | 24.54 | 22.64 |
| 5 | 10.96 | 38.12 | 19.14 | 26.14 |
| 6 | 8.78 | 38.60 | 24.41 | 25.35 |
| 7 | 4.31 | 44.56 | 31.95 | 18.55 |
| 8 | 10.44 | 44.93 | 23.22 | 23.22 |
| 9 | 11.14 | 47.40 | 21.92 | 18.36 |
| 10 | 10.56 | 46.89 | 23.34 | 17.74 |
| 11 | 10.66 | 48.12 | 23.45 | 16.61 |
| 12 | 9.86 | 48.38 | 24.40 | 16.34 |
| 13 | 10.95 | 49.35 | 22.32 | 15.22 |
| 14 | 11.11 | 50.16 | 22.65 | 14.31 |
| 15 | 1.23 | 36.56 | 49.62 | 11.26 |
| 16 | 10.52 | 50.68 | 24.02 | 12.53 |
| 17 | 10.10 | 51.90 | 23.82 | 11.86 |
| 18 | 10.59 | 54.41 | 23.65 | 10.23 |
| 19 | 11.23 | 53.75 | 22.11 | 10.77 |
| 20 | 9.81 | 52.94 | 23.40 | 10.94 |

This example demonstrates that these catalysts are useful in the liquid phase and are useful for the generation of acetic anhydride over multiple runs.

Although the present invention has been shown and described in terms of the presently preferred embodiments, it is to be understood that various modifications and substitutions, rearrangements of parts, components and process steps can be made by those skilled in the art without departing from the spirit and scope of the invention.

We claim:

1. A catalyst composition useful in carbonylation processes for producing esters, carboxylic acids, and carboxylic acid anhydrides from reactants including lower alkyl alcohols, ethers, esters, alcohol producing derivatives, olefins and mixtures thereof, said catalyst comprising a catalytically effective amount of an active metal selected from the group consisting of iron, cobalt, nickel, ruthenium, rhodium, palladium, osmium, iridium, platinum, tin and mixtures thereof associated with a support comprising carbonized polysulfonated divinylbenzene-styrene copolymer.

2. The composition of claim 1 wherein said catalyst includes from about 0.01 weight percent to about 10 weight percent of said active metal.

3. The composition of claim 1 wherein said catalyst includes from about 0.05 weight percent to about 5 weight percent of said active metal.

4. The composition of claim 1 wherein said catalyst includes from about 0.1 weight percent to about 2 weight percent of said active metal.

5. The composition of claim 1 wherein said active metal is Rh.

6. The composition of claim 1 wherein said active metal is Ir.

7. The composition of claim 1 further comprising a halogen promoting component selected from the group consisting of molecular halides selected from the group consisting of $I_2$, $Br_2$, and $Cl_2$, hydrogen halides, gaseous hydriodic acid, alkyl and aryl halides having up to 12 carbon atoms, and mixtures thereof.

8. The composition of claim 7 wherein said halogen promoting component is selected from the group consisting of hydrogen iodide, methyl iodide, ethyl iodide, 1-iodopropane, 2-iodobutane, 1-iodobutane, hydrogen bromide, methyl bromide, ethyl bromide, benzyl iodide and mixtures thereof.

9. The composition of claim 8 wherein said halogen promoting component is selected from the group consisting of hydrogen iodide, methyl iodide, hydrogen bromide, methyl bromide and mixtures thereof.

10. The composition of claim 1 further comprising a second metal selected from the group consisting of an alkali, an alkaline earth, lanthanides, gold, mercury, and transition metals selected from the group V, Nb, Ta, Ti, Zr, Hf, Mo, W, Re, and combinations thereof.

11. The composition of claim 10 wherein said second metal is selected from the group consisting of lanthanum, cerium, praseodymium, neodymium, and combinations thereof.

12. A catalyst composition useful in carbonylation processes for producing acetic acid, methyl acetate and acetic anhydride from methanol, methanol derivatives and mixtures thereof, said catalyst comprising from about 0.01 weight percent to about 10 weight percent of an active metal selected from the group consisting of iron, cobalt, nickel, ruthenium, rhodium, palladium, osmium, iridium, platinum, tin and mixtures thereof associated with a support comprising a carbonized polysulfonated divinylbenzene-styrene copolymer.

13. The composition of claim 12 wherein said catalyst includes from about 0.05 weight percent to about 5 weight percent of said active metal.

14. The composition of claim 12 wherein said catalyst includes from about 0.1 weight percent to about 2 weight percent of said active metal.

15. The composition of claim 12 wherein said active metal is selected from the group consisting of Rh and Ir.

16. The composition of claim 12 further comprising a halogen promoting component selected from the group consisting of molecular halides selected from the group consisting of $I_2$, $Br_2$, and $Cl_2$, hydrogen halides, gaseous hydriodic acid, alkyl and aryl halides having up to 12 carbon atoms, and mixtures thereof.

17. The composition of claim 16 wherein said halogen promoting component is selected from the group consisting of hydrogen iodide, methyl iodide, hydrogen bromide, methyl bromide and mixtures thereof.

18. The composition of claim 12 further comprising a second metal selected from the group consisting of an alkali, an alkaline earth, lanthanides, gold, mercury, and transition metals selected from the group V, Nb, Ta, Ti, Zr, Hf, Mo, W, Re, and combinations thereof.

19. A catalyst composition useful in a vapor-phase carbonylation process for producing acetic acid, methyl acetate and acetic anhydride from methanol, methanol derivatives and mixtures thereof, said catalyst comprising from about 0.01 weight percent to about 10 weight percent of an active metal selected from the group consisting of iron, cobalt, nickel, ruthenium, rhodium, palladium, osmium, iridium, platinum, tin and mixtures thereof and from about 0.01 weight percent to about 10 weight percent of a second metal selected from the group consisting of an alkali, an alkaline earth, lanthanides, gold, mercury, and transition metals selected from the group V, Nb, Ta, Ti, Zr, Hf, Mo, W, Re, and combinations thereof associated with a support comprising carbonized polysulfonated divinylbenzene-styrene copolymer.

20. The composition of claim 19 further comprising a halogen promoting component selected from the group consisting of hydrogen iodide, methyl iodide, hydrogen bromide, methyl bromide and mixtures thereof.

21. The composition of claim 20 wherein said active metal is selected from the group consisting of Rh, Ir and mixtures thereof and said second metal is selected from the group consisting of lanthanum, cerium, praseodymium, neodymium, and combinations thereof.

22. The composition of claim 20 wherein said catalyst includes from about 0.05 weight percent to about 5 weight percent of said active metal and said second metal.

23. The composition of claim 20 wherein said catalyst includes from about 0.1 weight percent to about 2 weight percent of said active metal and said second metal.

24. A method for preparing a solid supported catalyst composition useful for producing acetic acid, methyl acetate and acetic anhydride from methanol, methanol derivatives and mixtures thereof, said method comprising the steps of:

a. providing a carbonized polysulfonated divinylbenzene-polystyrene copolymer solid support material;

b. contacting said solid support material with a solution containing from about 0.01 weight percent to about 10 weight percent an active metal selected from the group consisting of iron, cobalt, nickel, ruthenium, rhodium, palladium, osmium, iridium, platinum, tin and mixtures thereof; and c. drying said solid support material wherein at least a portion of said soluble active is associated with the solid support material.

25. The method of claim 24 further comprising contacting said solid support material with a solution containing from about 0.01 weight percent to about 10 weight percent of a second metal selected from the group consisting of an alkali, an alkaline earth, lanthanides, gold, mercury, and transition metals selected from the group V, Nb, Ta, Ti, Zr, Hf, Mo, W, Re, and combinations thereof.

26. The method of claim 24 wherein said active metal is selected from the group consisting of Rh and Ir.

27. The method of claim 25 wherein said second metal is selected from the group consisting of lanthanum, cerium, praseodymium, neodymium, and combinations thereof.

* * * * *